(12) United States Patent
Fritz et al.

(10) Patent No.: US 11,148,901 B2
(45) Date of Patent: Oct. 19, 2021

(54) APPARATUS AND METHOD FOR APPLICATION OF DISCRETE MATERIAL SEGMENTS TO RUNNING WEB MATERIAL

(71) Applicant: Curt G. Joa, Inc., Sheboygan Falls, WI (US)

(72) Inventors: Jeffrey W. Fritz, Plymouth, WI (US); David E. Schuette, Kiel, WI (US); Justin M. Lafferty, Sheboygan, WI (US); Joram L. McClurg, Port Washington, WI (US); Todd A. Humphrey, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 16/571,377

(22) Filed: Sep. 16, 2019

(65) Prior Publication Data

US 2020/0095084 A1 Mar. 26, 2020

Related U.S. Application Data

(60) Provisional application No. 62/734,036, filed on Sep. 20, 2018.

(51) Int. Cl.
*B65H 35/00* (2006.01)
*A61F 13/00* (2006.01)
(Continued)

(52) U.S. Cl.
CPC ....... *B65H 35/08* (2013.01); *A61F 13/15642* (2013.01); *B32B 37/0053* (2013.01);
(Continued)

(58) Field of Classification Search
CPC ............... B65H 35/08; A61F 13/15642; B32B 37/0053; B32B 37/22; B32B 37/144;
(Continued)

(56) References Cited

U.S. PATENT DOCUMENTS

| 6,309,487 | B1 | 10/2001 | Herrin et al. |
| 7,713,371 | B2 | 5/2010 | Lohrengel et al. |
| 8,172,977 | B2 | 5/2012 | McCabe et al. |
| 8,221,380 | B2 | 7/2012 | Schmitz |

(Continued)

FOREIGN PATENT DOCUMENTS

GB 2530073 A 3/2016

*Primary Examiner* — Linda L Gray
(74) *Attorney, Agent, or Firm* — Ziolkowski Patent Solutions Group, SC (57) ABSTRACT

An apparatus and method for applying discrete segments to a continuous web includes feeding a first continuous web to a roller, the first continuous web comprising one or more layers, feeding a second continuous web to a vacuum anvil, cutting the first continuous web into a plurality of discrete segments via interaction of the roller with at least one cutting element selectively positionable adjacent the roller, transferring each of the plurality of discrete segments from the roller onto the second continuous web at a first location and via a vacuum pressure from the vacuum anvil, and bonding each of the plurality of discrete segments to the second continuous web at a second location downstream from the first location in a machine direction, each of the plurality of discrete segments bonded to the second continuous web via interaction of the vacuum anvil with a bonding device positioned at the second location.

19 Claims, 6 Drawing Sheets

(51) Int. Cl.
*B32B 37/00* (2006.01)
*B65H 35/08* (2006.01)
*A61F 13/15* (2006.01)
*B32B 37/22* (2006.01)

(52) U.S. Cl.
CPC .... *B32B 37/22* (2013.01); *A61F 2013/15869* (2013.01); *B32B 2555/00* (2013.01); *B65H 2406/33* (2013.01); *Y10T 156/1062* (2015.01); *Y10T 156/1077* (2015.01); *Y10T 156/1085* (2015.01); *Y10T 156/1092* (2015.01)

(58) Field of Classification Search
CPC ........... B32B 38/0004; Y10T 156/1062; Y10T 156/1077; Y10T 156/1085; Y10T 156/1092
See application file for complete search history.

(56) References Cited

U.S. PATENT DOCUMENTS

| | | | |
|---|---|---|---|
| 8,845,837 | B2 | 9/2014 | Tomsovic et al. |
| 9,162,432 | B2 * | 10/2015 | Schroeder ............... B26F 1/384 |
| 9,205,003 | B2 | 12/2015 | Tsang et al. |
| 9,211,217 | B2 | 12/2015 | Tomsovic et al. |
| 9,289,329 | B1 | 3/2016 | Schaap |
| 9,308,134 | B2 | 4/2016 | Wolter et al. |
| 9,433,538 | B2 | 9/2016 | Pagel et al. |
| 9,522,087 | B2 | 12/2016 | Tomsovic et al. |
| 9,603,750 | B2 | 3/2017 | Van De Maele |
| 9,622,918 | B2 | 4/2017 | McCabe et al. |
| 9,642,753 | B1 | 5/2017 | Andrews |
| 9,687,390 | B2 | 6/2017 | Davidson et al. |
| 9,849,041 | B2 | 12/2017 | Wolter et al. |
| 10,167,156 | B2 | 1/2019 | Ingole et al. |
| 10,456,302 | B2 | 10/2019 | Andrews et al. |
| 10,494,216 | B2 | 12/2019 | Pelland |
| 2013/0098545 | A1 | 4/2013 | Schroeder et al. |

* cited by examiner

APPARATUS AND METHOD FOR APPLICATION OF DISCRETE MATERIAL SEGMENTS TO RUNNING WEB MATERIAL

CROSS-REFERENCE TO RELATED APPLICATION

The present invention is a non-provisional of and claims priority to U.S. Provisional Patent Application Ser. No. 62/734,036, filed Sep. 20, 2018, the disclosure of which is incorporated herein by reference in its entirety.

BACKGROUND OF THE INVENTION

The present invention relates to disposable garments and more specifically, to systems and methods for making disposable garments. More specifically, the invention relates to ultrasonic bonding of garment layers. More specifically the invention relates to applying and bonding discrete segments such as, for example, segments of an acquisition distribution layer (ADL), to a continuous web.

Absorbent elements for disposable absorbent garments are commonly formed by different individual material layers which are superimposed, wherein each material layer is designed to provide specific properties. A typical structure for an absorbent garment includes a top sheet, an acquisition distribution layer (ADL), and a storage layer, and other layers can also be present such as a tissue layer, a layer to provide resiliency to the products, or a layer to provide a better visual impression, etc., as known in the art.

The ADL is typically placed on top of the body facing surface of the storage layer and serves the functions of rapidly acquiring the fluids excreted from the body and transferring them rapidly away from the body into the storage layer, and also keeping the storage layer separate enough from the skin so to prevent body fluids from rewetting the skin during the usage of the absorbent garment. The ADL also distributes the fluid on a larger surface area so to provide a more efficient usage of the surface of the storage layer.

Figure 1:
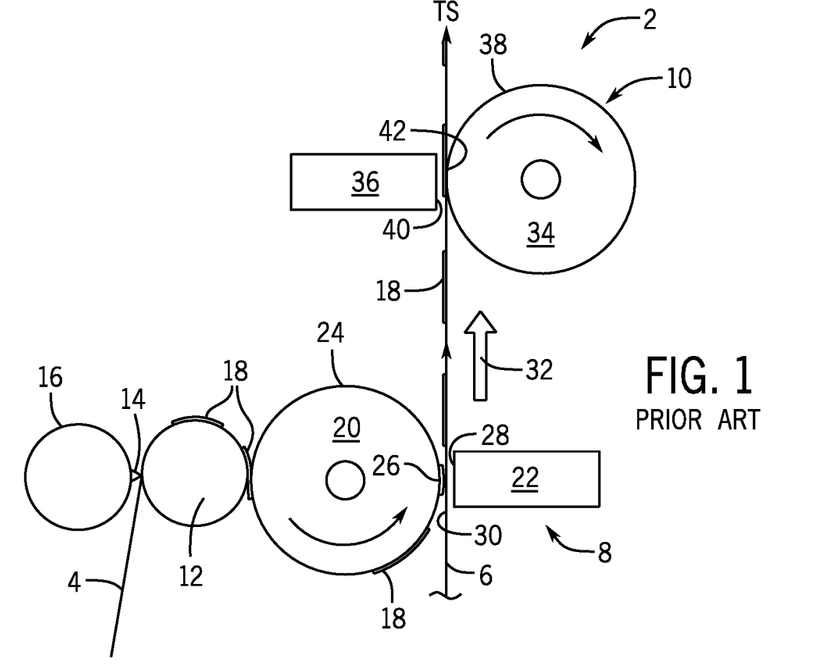
FIG. 1 is a side view of an apparatus for bonding an acquisition distribution layer (ADL) to a web, as known in the prior art.

With attention to FIG. 1, an apparatus 2 for bonding an ADL 4 to a web 6 (e.g., top sheet) during manufacturing of an absorbent garment is illustrated, according to a known prior art implementation. The apparatus 2 comprises a first anvil/blade horn assembly 8 and a second anvil/blade horn assembly 10 in linear succession that function to bond the ADL 4 to the web 6.

A continuous feed of ADL 4 is fed onto a surface of a receiving anvil 12 and is subsequently cut by a knife 14 on a knife wheel 16 to form discrete ADL sections 18. The discrete ADL sections 18 are maintained on receiving anvil 12 and rotate thereabout to a location where they are transferred to an anvil 20 that is part of first anvil/blade horn assembly 8. The discrete ADL sections 18 are maintained on anvil 20 and rotate thereabout to a location adjacent a blade horn 22 that is part of first anvil/blade horn assembly 8. Extending from a surface 24 of the anvil 20 is an anvil insert or pattern 26 that interacts with a surface 28 of blade horn 22 to tack bond the ADL section 18 to the web 6.

In operation, the web 6 proceeds between the anvil surface 24 and the blade horn surface 28 of the first anvil/blade horn assembly 4, such that a web top surface 30 is in proximity to the anvil surface 24 of the anvil 20 of the first anvil/blade horn assembly 4. Discrete ADL sections 18 are brought into close communication with the web top surface 30 via rotation of anvil 20, and the discrete ADL sections 18 and web 6 are then tack bonded to one another by first anvil/blade assembly 8 via interaction of the blade horn 22 with the anvil surface 24. The tack bonded ADL sections 18 and web 6 then proceed linearly 32 to the second anvil/blade horn assembly 10.

The second anvil/blade assembly 6 comprises an anvil 34 and a blade horn 36, with the anvil 34 comprising an anvil surface 38 and the blade horn 36 comprising a blade horn surface 40. The web 6 and the ADL sections 18 proceed to location 44 between the anvil surface 38 and the blade horn surface 40 of the second anvil/blade horn assembly 10, such that the web top surface 30 and the ADL sections 18 are in proximity to the blade horn surface 40. An ultrasonic bond (not illustrated in the figures) is created at location 42 where blade horn surface 40 interacts with anvil surface 38, thus bonding the ADL 4 to the web 6.

During operation of apparatus 2, the ADL sections 18 may inadvertently become detached from the web 6 if the tack bond formed by first anvil/blade assembly 8 is not sufficient to maintain the ADL sections 18 on the web 6 during transfer from the first anvil/blade assembly 8 to the second anvil/blade horn assembly 10 and/or during bond formation at the second anvil/blade horn assembly 10. Accordingly, a need exists for an improved apparatus and method for applying discrete segments of a material, such as an ADL, onto a web. Such an apparatus and method would, according to exemplary embodiments, utilize a single ultrasonic horn and anvil assembly, utilize a rotary ultrasonic horn, utilize a vacuum to promote continued placement of the discrete segments on the web in a secure fashion, and/or utilize a roller for application of discrete segments to a web.

BRIEF DESCRIPTION OF THE INVENTION

In accordance with one aspect of the invention, a method for applying discrete segments to a continuous web includes feeding a first continuous web to a roller, the first continuous web comprising one or more layers, feeding a second continuous web to a vacuum anvil, cutting the first continuous web into a plurality of discrete segments via interaction of the roller with at least one cutting element selectively positionable adjacent the roller, transferring each of the plurality of discrete segments from the roller onto the second continuous web at a first location and via a vacuum pressure from the vacuum anvil, and bonding each of the plurality of discrete segments to the second continuous web at a second location downstream from the first location in a machine direction, each of the plurality of discrete segments bonded to the second continuous web via interaction of the vacuum anvil with a bonding device positioned at the second location.

In accordance with another aspect of the invention, an apparatus for applying discrete segments to a continuous web includes a roller rotating to translate a first continuous web along a roller surface of the roller, the first continuous web comprising one or more layers. The apparatus also includes a vacuum anvil rotating to translate a second continuous web along an anvil surface of the vacuum anvil, the roller and vacuum anvil adjacent to one another at a first location. The apparatus further includes at least one cutting element selectively positionable adjacent the roller and that interacts with the roller to cut the first continuous web into a plurality of discrete segments and a bonding device operable with the vacuum anvil to bond each of the plurality of discrete segments to the second continuous web at a second location downstream from the first location in a machine direction in which the plurality of discrete segments and the second continuous web are translated, wherein the roller rotates to translate the plurality of discrete segments to the first location, after being cut by the interaction of the at least one knife and the roller, and wherein the vacuum anvil generates a vacuum pressure at the anvil surface to cause each of the plurality of discrete segments to transfer from the roller onto the second continuous web at the first location and to be held in place on the second continuous web.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the present invention provide for a method and apparatus for applying a discrete segment of material a continuous web. An arrangement of rolls or wheels, including a vacuum anvil, are utilized in combination with a bonding tool to provide a method for applying the discrete segment to a running web, to promote continued placement of the discrete segment thereon. In the embodiments described herein, the discrete segment is an acquisition distribution layer (ADL). However, the method and apparatus can used to apply other types of discrete segments to a continuous web, including extension panels and ear segments as non-limiting examples.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined in the specification.

Figure 2:
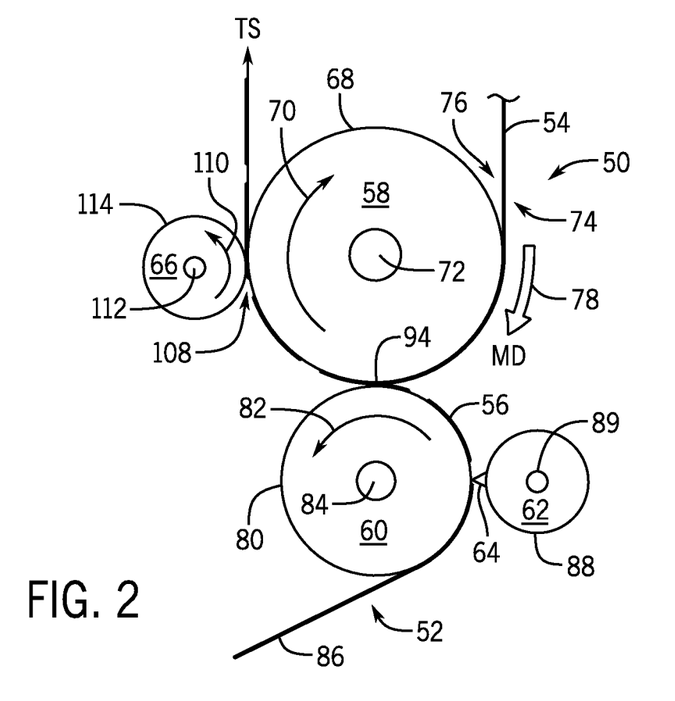
FIG. 2 is a side view of an apparatus for applying discrete segments of material, such as segments of an ADL, to a continuous web, according to an embodiment of the invention.

Referring first to FIG. 2, a side view of an apparatus 50 for bonding an ADL 52 to a web 54 is illustrated, with the apparatus 50 comprising a rotary-type apparatus according to an exemplary embodiment of the invention. The apparatus 50 operates to provide a continued placement of a plurality of discrete ADL segments 56 onto the web 54 and maintain the ADL segments 56 in place on the web 54 while advancing the ADL segments 56 and the web 54 and while forming bonds between the ADL segments 56 and the web 54.

With regard to the materials used in the ADL 52 and web 54, ADL 52 is constructed of material(s) configured to quickly acquire fluid and distribute fluid in an efficient manner. Web 54 is—in an exemplary embodiment—a top sheet constructed of any of a number of suitable materials capable of fusing to the ADL 52 upon application of an applied energy that causes one or both of the layers/webs to soften or melt and join together. As non-limiting examples, web 54 may be comprised of nonwoven materials, woven materials, films, and/or composites or laminates of any of these material types.

With regard to ADL 52, while the ADL 52 is shown in FIG. 2 generally as a single layer of material, it is recognized that the ADL 52 may comprise one, two, or more layers, which may form a unitary layer or remain discrete layers which may be attached to each other. In an exemplary embodiment, the ADL 52 comprises two layers: a distribution layer and an acquisition layer, but embodiments of the ADL 52 are not restricted to this example. The distribution layer and acquisition layer will now be exemplified in more details.

The distribution layer may, for example, comprise at least 50% by weight of cross-linked cellulose fibers. The cross-linked cellulosic fibers may be crimped, twisted, or curled, or a combination thereof including crimped, twisted, and curled. The cross-linked cellulosic fibers provide higher resilience against the compression in the product packaging or in use conditions, e.g. under baby weight. The distribution layer comprising cross-linked cellulose fibers may comprise other fibers, but this layer may advantageously comprise at least 50%, or 60%, or 70%, or 80%, or 90% or even up to 100%, by weight of the layer, of cross-linked cellulose fibers (including the cross-linking agents). An example of such a mixed layer of cross-linked cellulose fibers may comprise about 70% by weight of chemically cross-linked cellulose fibers, about 10% by weight polyester (PET) fibers, and about 20% by weight untreated pulp fibers.

The acquisition layer may typically be or comprise a non-woven material, for example a SMS or SMMS material, comprising a spunbonded, a melt-blown and a further spun-bonded layer or alternatively a carded chemical-bonded nonwoven. The non-woven material may in particular be latex bonded, with an exemplary binder being a stabilized by a latex binder such as a styrene-butadiene latex binder (SB latex), for example. A further acquisition layer may be used in addition to a first acquisition layer described above. For example, a tissue layer may be placed between the first acquisition layer and the distribution layer. The tissue may have enhanced capillarity distribution properties compared to the acquisition layer described above.

As shown in FIG. 2, apparatus 50 generally comprises a vacuum anvil 58, a roller 60, a cutting element 62 (which in the illustrated embodiment comprises a knife wheel 62 having one or more knives 64 thereon), and a bonding device 66. In the illustrated embodiment, apparatus 50 comprises a rotary-type assembly in that each of vacuum anvil 58, roller 60, knife wheel 62, and bonding device 66 comprises a rotary device that rotates about a respective axis of rotation. It is recognized, however, that one or more of the devices could be a non-rotary type device, such as cutting element and/or bonding device alternatively being a non-rotary type device. Thus, embodiments of the invention are not meant to be limited to the specific apparatus 50 illustrated in FIG. 2.

The vacuum anvil 58 comprises a rotary anvil having an anvil surface 68 rotating in a first direction 70 about a vacuum anvil center of rotation 72. A continuous top sheet web 54 having a first surface 74 and a second surface 76 is fed onto the vacuum anvil 58 and traverses along the vacuum anvil surface 68 in a machine direction (MD) 78, such that the second surface 76 is in direct communication with the vacuum anvil surface 68. As will be explained/illustrated in greater detail below, vacuum anvil 58 is a generally cylindrical body connected to a source of vacuum, with the vacuum anvil 58 including a plurality of vacuum holes on the anvil surface 68 in communication with the vacuum source. A vacuum may thus be selectively provided on the anvil surface 68 in order to retain the top sheet web 54 thereon, as well as to attract and maintain discrete ADL segments onto the top sheet web 54, as will be explained in greater detail below.

The roller 60 comprises a roller surface 80 rotating in a second direction 82 (opposite first direction 70) about a roller axis of rotation 84. A continuous web 86 of ADL 52 is fed onto the roller 60 and traverses along the roller surface 80 in machine direction 78, such that the continuous ADL web 86 is in direct communication with the roller surface 80. Roller 60 is configured to retain the continuous ADL web 86 thereon, as well as to maintain discrete ADL segments 56 thereof subsequent to cutting of the ADL web 86, as will be explained in greater detail below. According to embodiments, roller may thus be configured as a vacuum roller that selectively provides a vacuum pressure on the roller surface 80 in order retain the continuous ADL web 86 and/or ADL segments 56 thereon, but could alternatively retain the continuous ADL web 86 and/or ADL segments 56 thereon via alternative means, such as friction, etc.

Figure 3:
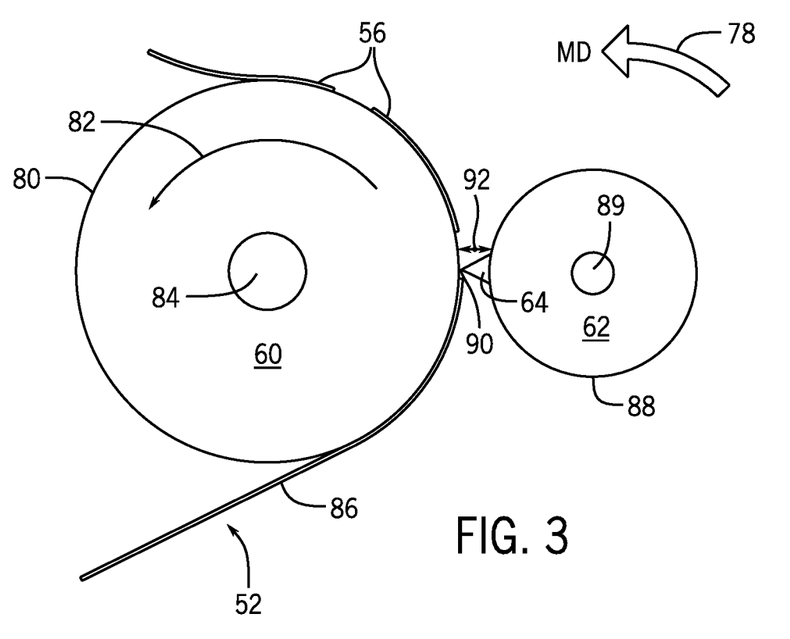
FIG. 3 is a side view of a roller and knife wheel included in the apparatus illustrated in FIG. 2, according to an embodiment of the invention.
Figure 4:
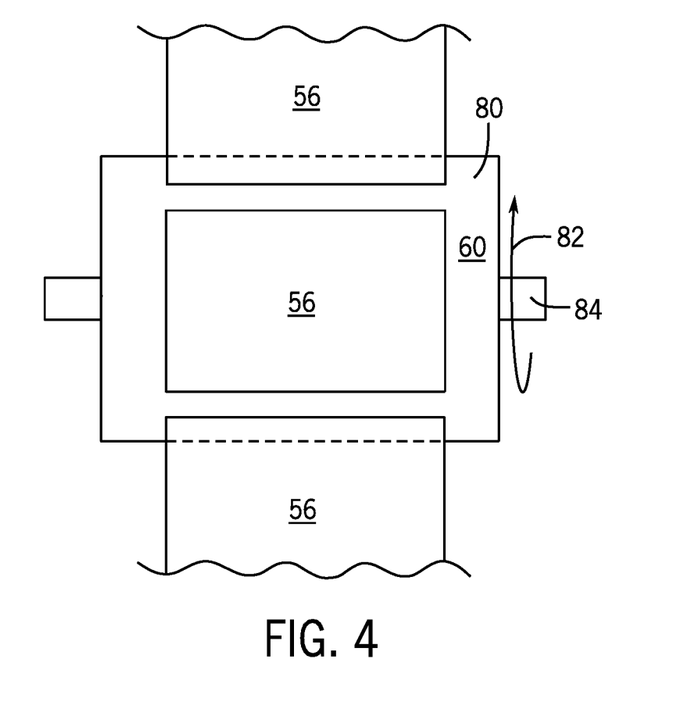
FIG. 4 is a top view of a roller included in the apparatus illustrated in FIG. 2, illustrating a continuous ADL web and an ADL section traversing along a surface of the roller.

As can be seen in FIG. 2, and also in FIG. 3, the roller 60 is positioned proximate to knife wheel 62, such that roller 60 may interact with knife wheel 62 to cut the continuous ADL web 86. As best shown in FIG. 3, the knife wheel 62 comprises a knife wheel surface 88 rotating about a knife wheel center of rotation 89, with at least one knife 64 being in fixed communication with the knife wheel surface 88. Alternatively, the at least one knife 64 is in removable communication with the knife wheel surface 88. The knife wheel 62 is positioned in close proximity to the roller surface 80 such that a knife apex 90 extending a distance 92 from the knife wheel surface 88 is in periodic and releasable communication with the roller surface 80, such that the knife 64 acts to perform a cut on the continuous ADL web 86. The releasable communication between the knife apex 90 and the roller surface 80 repeats with every communication of a knife apex 90 and the roller surface 80, such that multiple cuts are performed on the continuous ADL web 86 to form discrete ADL segments 56, such as shown in greater detail in FIG. 4. After cutting, the discrete ADL segments 56 continue to rotate about roller 60 while being maintained on the roller surface 80, such as via a vacuum or friction provided on the roller surface 80.

As shown in FIG. 2, the interaction of the knife wheel 62 and the roller 60 that forms discrete ADL segments 56 is upstream of a first location 94 where the roller 60 is in rotating and tangential communication with the vacuum anvil 58. In operation of apparatus 50, the top sheet web 54 traverses about along the vacuum anvil surface 68 in the machine direction 78 to the first location 94, while discrete ADL segments 56 traverse about along the roller surface 80 in the machine direction 78 to the first location 94. At the first location 94, a vacuum pressure generated by vacuum anvil 58 encourages the top sheet web 54 to maintain communication with the vacuum anvil surface 68 and also encourages a discrete ADL segment 56 to be drawn off of roller surface 80 and onto the second surface 106 of the top sheet web 54.

Figure 5:
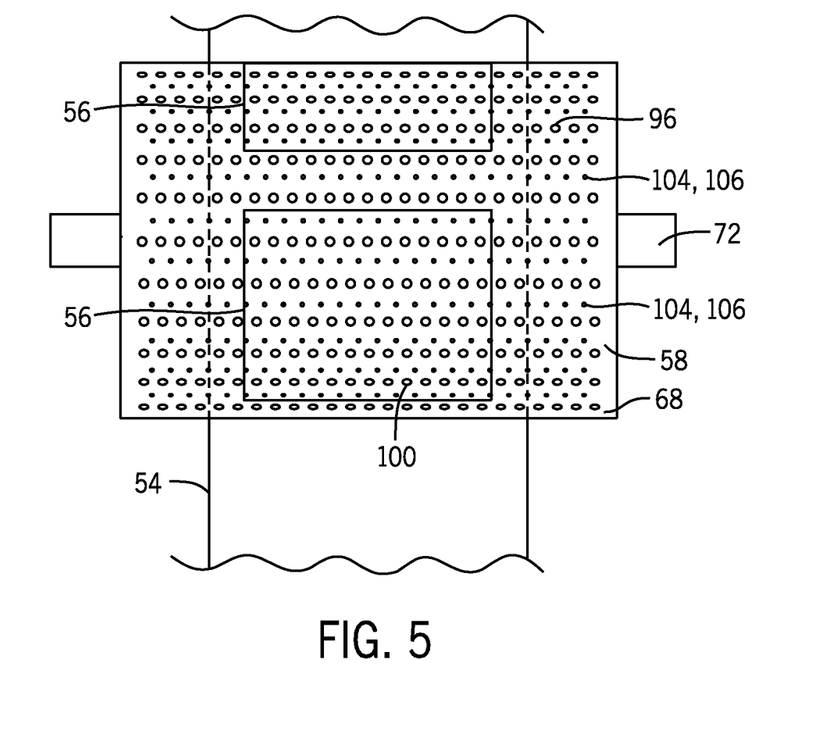
FIG. 5 is a top view of a vacuum anvil included in the apparatus illustrated in FIG. 2, according to an embodiment of the invention.
Figure 6:
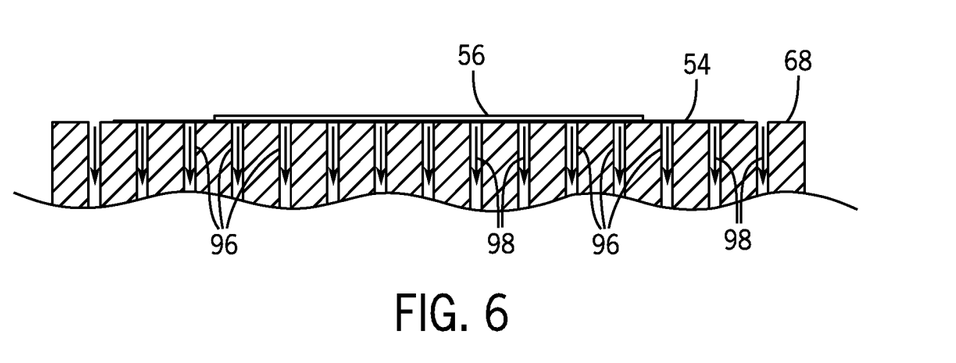
FIG. 6 is a cross-section of a vacuum anvil surface of the vacuum anvil illustrated in FIG. 5.
Figure 7:
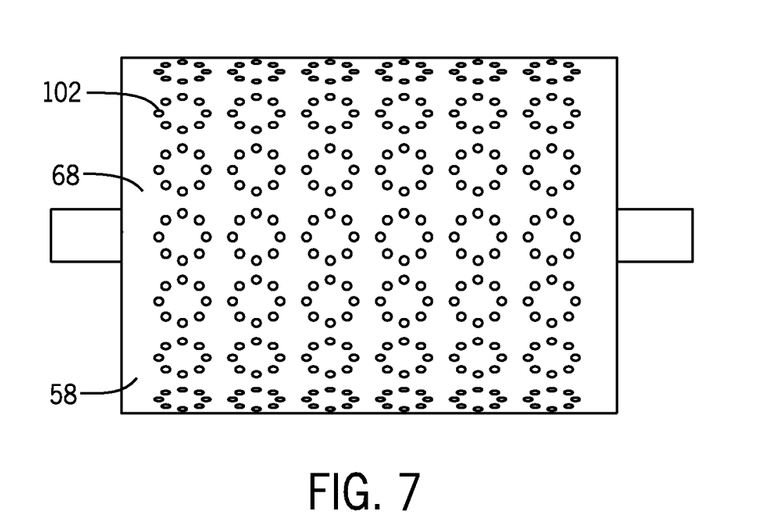
FIG. 7 is a top view of a vacuum anvil included in the apparatus illustrated in FIG. 2, according to another embodiment of the invention.

The structure of vacuum anvil 58 is shown in more detail in FIGS. 5-7. In the illustrated embodiment(s), vacuum anvil surface 68 includes a plurality of vacuum holes 96 extending through the vacuum anvil surface 68 and into an interior of the vacuum anvil 58. The vacuum holes 96 provide for a vacuum pressure 98 that encourages the top sheet web 54 to maintain communication with the vacuum anvil surface 68 and encourages the ADL segments 56 to commence communication with the second surface 74 of the top sheet web 54. The vacuum holes 96 may comprise a pattern of rows 100 on the vacuum anvil surface 68 (FIG. 5) or alternatively may comprise a plurality of circular patterns 102 on the vacuum anvil surface 68 (FIG. 7). According to still other embodiments, the vacuum holes 96 on the vacuum anvil surface 68 may comprise a pattern that generally matches the shape of the ADL segments 56 and a placement location of the ADL segments 56 on the vacuum anvil 58. In an embodiment where the pattern of vacuum holes 96 generally matches the shape and placement locations of the ADL segments 56, the coverage or zones formed by the pattern of vacuum holes 96 may be sized so as to be slightly larger than the ADL segments 56.

As further shown in FIG. 5, the vacuum anvil surface 68 further comprises a plurality of raised features/protrusions 104 extending from the vacuum anvil surface 68 in a radial direction 105 (FIG. 8) away from the vacuum anvil center of rotation 72. The plurality of raised features/protrusions 104 preferably form a raised pattern 106 which coincidences/matches with the pattern of the vacuum holes 96. Alternatively, the raised pattern 106 may be a pattern oriented/arranged independent of the pattern of the vacuum holes 96. The raised pattern 106 may comprise a plurality of rows on the vacuum anvil surface 68, as shown in FIG. 5, or alternatively may comprise circles, polygons, ovals, or shapes generally matching the shape of the ADL segments 56. In alternative embodiments, the raised features/protrusions 104 may be omitted.

Figure 8:
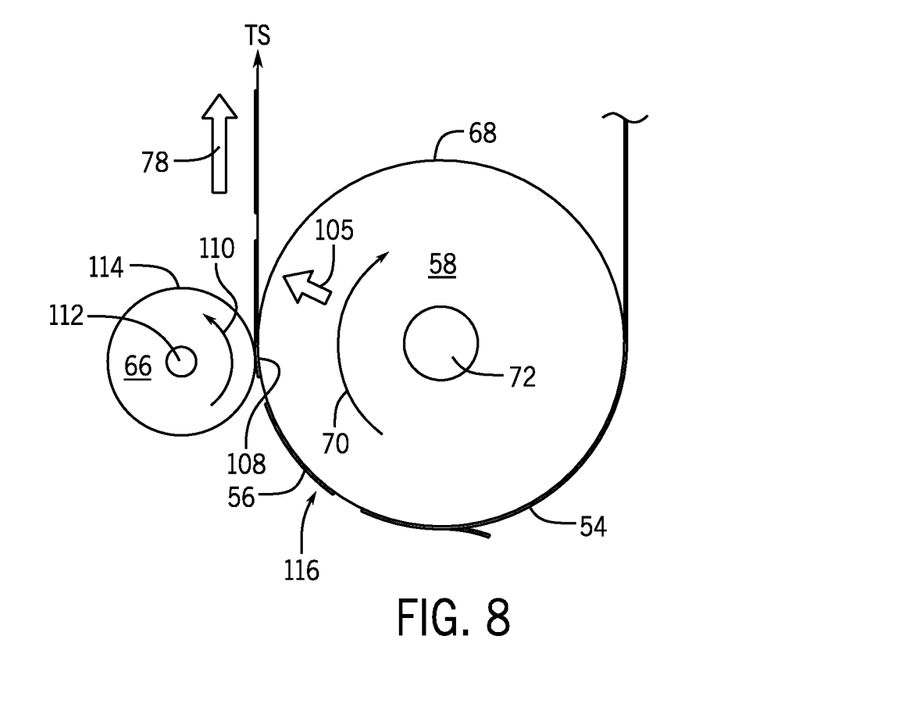
FIG. 8 is a side view of a vacuum anvil and at least one horn included in the apparatus illustrated in FIG. 2, according to an embodiment of the invention.

Referring again to FIG. 2 and now also to FIG. 8, and as shown therein, the configuration of bonding device 66 and placement thereof relative to vacuum anvil 58 provides for a bonding operation to be performed on the ADL segments 56 and top sheet web 54. The vacuum anvil 58 is in rotating and tangential communication with bonding device 66 at a second location 108 that is downstream in the machine direction 78 from the first location 94. According to some embodiments of the invention, vacuum anvil 58 and bonding device 66 are configured as an ultrasonic bonding assembly that ultrasonically fuses the ADL segments 56 to top sheet web 54. In such embodiments, bonding device 66 may be a rotary ultrasonic horn or a blade ultrasonic horn, for example. Where bonding device 66 is a rotary ultrasonic horn (rotating in direction 110 about axis 112), bonding device 66 cooperates with the rotary vacuum anvil 58 to bond the ADL segments 56 to top sheet web 54. Associated with the horn 66 are one or more frames (not shown) that support and/or house a motor (not shown) that drives the horn 66, and a vibration control unit (not shown) that causes the horn 66 to vibrate.

While bonding device 66 is referred to hereafter as a horn configured for ultrasonic bonding, it is contemplated that the techniques described herein may be extended to any other known welding or bonding techniques that fuse together two or more material layers. In such alternative embodiments, bonding device 66 would be constructed to cooperate with anvil 58 in a manner that couples ADL segments 56 to top sheet web 54 via sonic, thermal, or pressure bonding techniques, or other forms of welding known in the industry. In yet other embodiments, apparatus 50 may include an adhesive applicator (not shown) that applies adhesive to the ADL segments 56 and/or select locations of the top sheet web 54.

As shown in FIG. 8, the horn 66 and vacuum anvil 58 are positioned in a spaced relationship relative to one another to facilitate ultrasonically bonding the ADL segments 56 and the top sheet web 54. The surface 114 of the horn 66 is in removable and rotating communication with the raised pattern 106 on vacuum anvil 58. When a web/ADL segment combination 116 held on vacuum anvil 58 rotates through the second location 108, the ADL segment 56 is ultrasonically bonded to the top sheet web 54 pursuant to the raised pattern 106. The ultrasonically bonded top sheet web 54 and ADL segment 56, i.e., web/ADL segment combination 116, then proceeds along the machine direction 78 away from second location 108.

Figure 9:
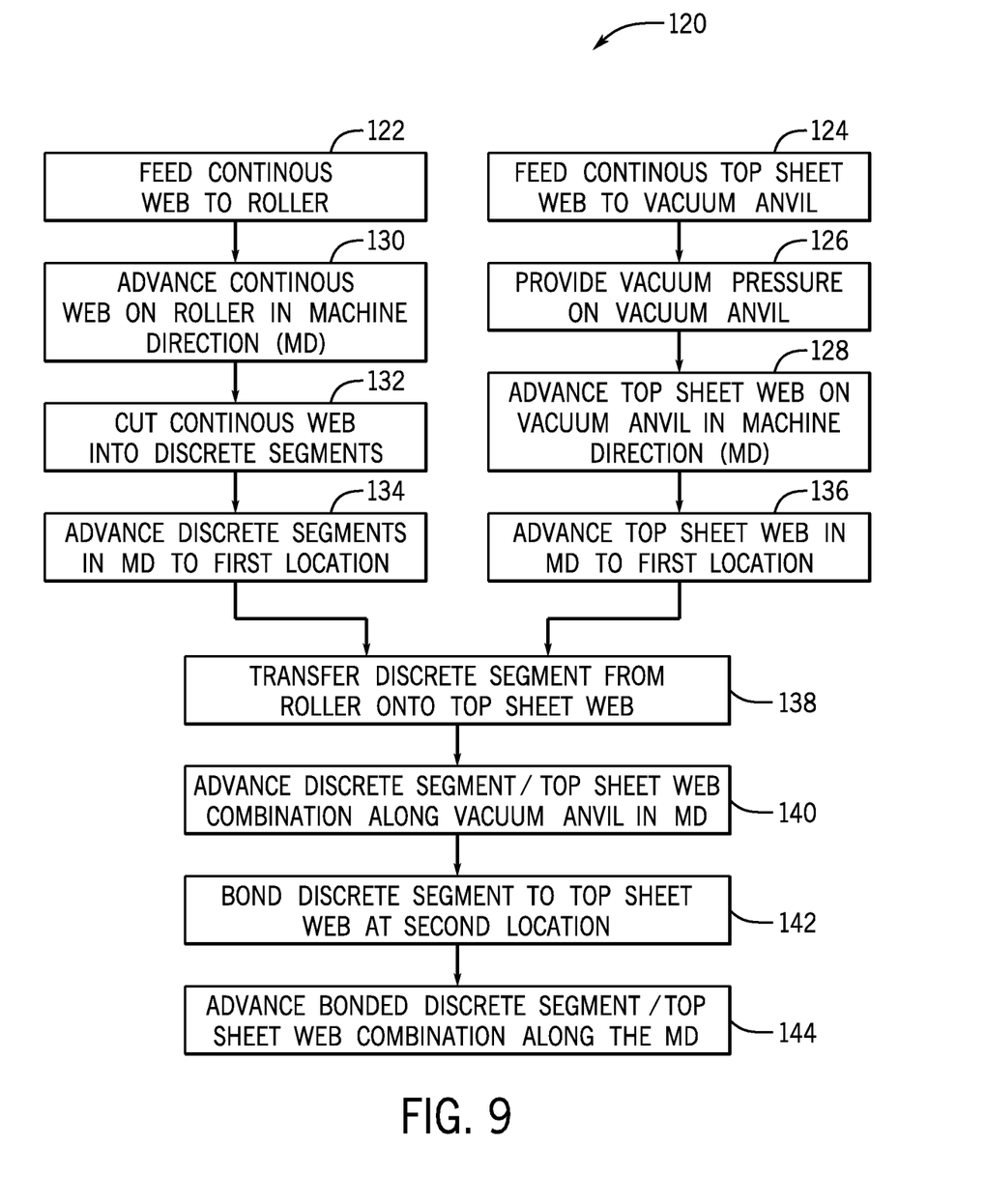
FIG. 9 is a flowchart illustrating a method for applying discrete segments of material to a continuous web, according to an embodiment of the invention.

Referring now to FIG. 9, a technique 120 for applying discrete segments to a continuous web is illustrated, according to an embodiment of the invention. Technique 120 may be used to apply discrete ADL segments (comprising one or more layers—acquisition layer, distribution layer, etc.) or other types of discrete segments (extension panels, ears, and the like). The technique 120 may be performed via operation of the apparatus 50 of FIG. 2, for example.

As shown in FIG. 9, technique 120 begins at STEPS 122 and 124 by feeding a continuous first web 86 to roller 60 and a continuous top sheet web 54 to vacuum anvil 58, respectively. The continuous first web 86 and continuous top sheet web 54 may be fed via any of a number of known feed devices and provided at a desired velocity and tension, such as via the use of festoons or accumulators, for example. As indicated at STEP 126, a vacuum pressure is provided on the vacuum anvil 58 to maintain the continuous top sheet web 54 on the surface 68 of vacuum anvil 58. Rotation of the vacuum anvil 58 (in first direction 70) causes the continuous top sheet web 54 to advance in machine direction 78, as indicated at STEP 128, while rotation of the roller 60 (in second direction 82) causes the continuous first web 86 to advance in machine direction 78, as indicated at STEP 130.

In a next STEP 132 of technique 120, the continuous first web 86 is then cut into a plurality of discrete segments 56. In cutting the continuous first web 86, the web 86 advances along the rotating roller 60 to a location that is adjacent a cutting element 62, such as a knife wheel 62 for example. A knife 64 included on knife wheel 62 then interacts with roller 60—i.e., a knife apex 90 extending a distance 92 from the knife wheel surface 88 comes into releasable communication with the roller surface 80—to cut the continuous first web 86. After cutting, a discrete segment 56 continues to rotate about roller 60 while being maintained on the roller surface 80 at STEP 134, such as via a vacuum provided on the roller surface 80 or other means of retaining the discrete segment 56 on the roller surface 80. The discrete segment 56 is thus advanced in the machine direction 78 to first location 94, which is the location where roller 60 is in tangential arrangement with vacuum anvil 58. As the discrete segment 56 is advancing on roller at STEP 134, continuous top sheet web 54 is also advanced in the machine direction 78 at STEP 136 by rotation of vacuum anvil 58. The continuous top sheet web 54 is thus also advanced in the machine direction 78 to first location 94.

Upon a discrete segment 56 being advanced on roller 60 to the first location 94, the discrete segment 56 is transferred off of the roller 60 and onto the continuous top sheet web 54 that is on the anvil surface 68 of vacuum anvil 58, as indicated at STEP 138. In transferring the discrete segment 56 off of the roller 60 and onto the continuous top sheet web 54, a vacuum pressure or suction force generated by/present on the vacuum anvil 58 draws the discrete segment 56 off of the roller 60 and onto the continuous top sheet web 54. The vacuum pressure is strong enough to draw the discrete segment 56 off of the roller 60 and onto the continuous top sheet web 54 and to also maintain the discrete segment 56 in position on the continuous top sheet web 54 upon completion of the transfer. With regard to the transfer of the discrete segment 56, the transfer can be characterized as a rolled application of the discrete segment 56 onto the continuous top sheet web 54, as the discrete segment 56 is gradually drawn off of the roller 60 and applied onto the continuous top sheet web 54 as the discrete segment 56 progresses through the first location 94.

Once a discrete segment 56 is applied onto the continuous top sheet web 54, the technique 120 continues at STEP 140 with the web/discrete segment combination 116 advanced in the machine direction 78 by rotation of vacuum anvil 58 and maintained on the anvil surface 68 via the vacuum pressure present thereon. The web/discrete segment combination 116 is advanced from the first location 94 to the second location 108—where horn 66 is positioned adjacent to the vacuum anvil 58. Upon reaching the second location 108, the discrete segment 56 is bonded to the continuous top sheet web 54 at STEP 142. According to an exemplary embodiment, horn 66 comprises a rotary ultrasonic horn that cooperates with the rotary vacuum anvil 58 to bond the discrete segment 56 to top sheet web 54. The surface 114 of the rotary horn 66 is in removable and rotating communication with the raised pattern 106 on vacuum anvil 58. When the combined discrete segment 56 and continuous top sheet web 54 held on vacuum anvil 58 rotates through the second location 108, the discrete segment 56 is ultrasonically bonded to the top sheet web 54 pursuant to the raised pattern 106. The ultrasonically bonded top sheet web 54 and discrete segment 56, i.e., web/discrete segment combination 116, then proceeds along the machine direction 78 away from second location 108, as indicated at STEP 144.

Figure 10:
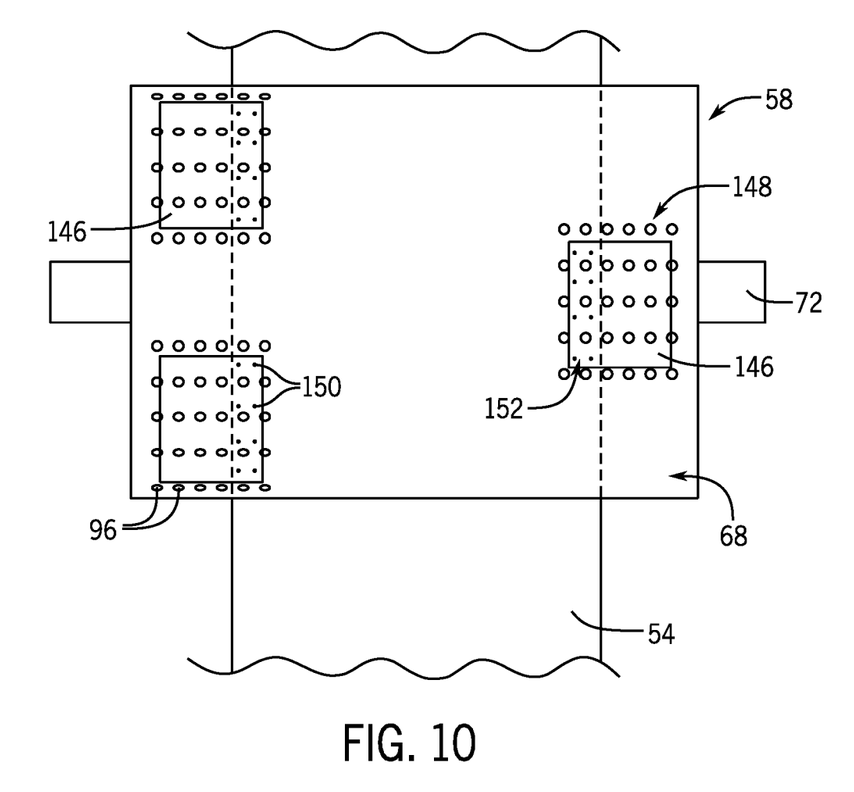
FIG. 10 is a top view of a vacuum anvil useable in the apparatus illustrated in FIG. 2 for applying ear segments to a continuous web, according to another embodiment of the invention.

According to another embodiment, and as previously indicated above, a method and apparatus may be provided to apply other various types of discrete segments to a continuous web. Referring now to FIG. 10, and with reference also back to the apparatus and method of FIGS. 2 and 10, an embodiment of a vacuum drum 58 is illustrated that could be incorporated into the apparatus 50 of FIG. 2 and/or the technique 120 of FIG. 10, for bonding ear segments 146 to the web 54. As shown in FIG. 9, the vacuum anvil 58 includes an anvil surface 68 that comprises a plurality of vacuum holes 96 extending through the vacuum anvil surface 68 and into an interior of the vacuum anvil 58. The vacuum holes 96 provide for a vacuum pressure 98 that encourages the top sheet web 54 to maintain communication with the vacuum anvil surface 68 and encourages the ear segments 146 to commence communication with the second surface 74 of the top sheet web 54. The vacuum holes 96 are formed in anvil surface 68 in a pattern 148 that generally matches the shape and placement location of the ear segments 146, with the coverage or zones formed by the pattern 148 of vacuum holes 96 being sized so as to be slightly larger than the ear segments 146. As further shown in FIG. 9, the vacuum anvil surface 68 also comprises a plurality of raised features/protrusions 150 extending from the vacuum anvil surface 68 in a radial direction 105 (FIG. 8) away from the vacuum anvil center of rotation 72. The plurality of raised features/protrusions 150 form a raised pattern 152 that, according to the illustrated embodiment, cover the area that the ear segments 146 overlap with the top sheet web 54. In alternative embodiments, the raised features/protrusions 104 may be omitted.

In applying discrete ear segments 146 to the web 54, the ear segments 146 would first be cut from a continuous first web 86 of ear web material that is provided on roller 60—with it being recognized that a single first web 86 of ear web material may be provided to form the ear segments 146 or that separate first webs 86 of ear web material may be provided to form the ear segments 146, either on a single roller 60 or separate rollers 60. The cutting of first web 86 to form ear segments 146 is performed by a cutting element 62 that may comprise a knife wheel or a die cut element, for example. The cut ear segments 146 are then translated along roller(s) 60 to the first location 94, where the ear segments 146 are caused to be drawn onto web 54 via a vacuum pressure provided through the pattern 148 of vacuum holes 96 on the anvil surface 68 illustrated in FIG. 10. The ear segments 146 are then retained on web 54 and translated to the second location 108, where the ear segments 146 are bond to the web 54 as previously explained in detail above.

Beneficially, embodiments of the invention thus provide an apparatus and method for applying and bonding discrete segments cut from a continuous web—to a continuous web, such as a top sheet web. The application and bonding are achieved via a rotary-type application and bonding apparatus that utilizes only a single horn and anvil combination/assembly, so as to reduce costs of the apparatus as compared to existing apparatuses that utilize two horn and anvil combinations/assemblies. Discrete segments are transferred from a rotating roller onto a rotating vacuum anvil that is in tangential communication with roller, with a vacuum pressure present on the vacuum anvil causing the discrete segments to be drawn off of the roller and transferred onto the top sheet web. The vacuum pressure is sufficient to hold the top sheet web and discrete segment in place on the surface of the vacuum anvil, without the possibility of the discrete segment peeling off and/or shifting on the top sheet web. Discrete segments are then bonded to the top sheet web via interaction of a (rotary) ultrasonic horn with the vacuum anvil.

Therefore, according to one embodiment of the invention, a method for applying discrete segments to a continuous web includes feeding a first continuous web to a roller, the first continuous web comprising one or more layers, feeding a second continuous web to a vacuum anvil, cutting the first continuous web into a plurality of discrete segments via interaction of the roller with at least one cutting element selectively positionable adjacent the roller, transferring each of the plurality of discrete segments from the roller onto the second continuous web at a first location and via a vacuum pressure from the vacuum anvil, and bonding each of the plurality of discrete segments to the second continuous web at a second location downstream from the first location in a machine direction, each of the plurality of discrete segments bonded to the second continuous web via interaction of the vacuum anvil with a bonding device positioned at the second location.

According to another embodiment of the invention, an apparatus for applying discrete segments to a continuous web includes a roller rotating to translate a first continuous web along a roller surface of the roller, the first continuous web comprising one or more layers. The apparatus also includes a vacuum anvil rotating to translate a second continuous web along an anvil surface of the vacuum anvil, the roller and vacuum anvil adjacent to one another at a first location. The apparatus further includes at least one cutting element selectively positionable adjacent the roller and that interacts with the roller to cut the first continuous web into a plurality of discrete segments and a bonding device operable with the vacuum anvil to bond each of the plurality of discrete segments to the second continuous web at a second location downstream from the first location in a machine direction in which the plurality of discrete segments and the second continuous web are translated, wherein the roller rotates to translate the plurality of discrete segments to the first location, after being cut by the interaction of the at least one knife and the roller, and wherein the vacuum anvil generates a vacuum pressure at the anvil surface to cause each of the plurality of discrete segments to transfer from the roller onto the second continuous web at the first location and to be held in place on the second continuous web.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method for applying discrete segments to a continuous web, the method comprising:
    feeding a first continuous web to a roller, the first continuous web comprising one or more layers;
    feeding a second continuous web to a vacuum anvil, the vacuum anvil comprising:
        a plurality of vacuum holes formed in an anvil surface through which a vacuum pressure is communicated; and
        a plurality of raised protrusions extending out from the anvil surface;
    cutting the first continuous web into a plurality of discrete segments via interaction of the roller with at least one cutting element selectively positionable adjacent the roller;
    transferring each of the plurality of discrete segments from the roller onto the second continuous web at a first location, the plurality of discrete segments being transferred onto the second continuous web via the vacuum pressure from the vacuum anvil; and
    bonding each of the plurality of discrete segments to the second continuous web at a second location downstream from the first location in a machine direction, each of the plurality of discrete segments bonded to the second continuous web via interaction of the plurality of raised protrusions of the vacuum anvil with a bonding device positioned at the second location to form a pattern of bonds between the second continuous web and respective discrete segments of the plurality of discrete segments.

2. The method of claim 1 wherein bonding each of the plurality of discrete segments to the second continuous web comprises causing an ultrasonic horn of the bonding device to interact with the vacuum anvil at the second location to ultrasonically bond the discrete segment to the second continuous web.

3. The method of claim 1 wherein feeding the first continuous web comprises feeding a continuous acquisition distribution layer; and wherein bonding each of the plurality of discrete segments to the second continuous web comprises bonding discrete acquisition distribution layer segments to the second continuous web.

4. The method of claim 1 wherein, in bonding each of the plurality of discrete segments to the second continuous web, the second continuous web is adjacent the vacuum anvil and a respective discrete segment of the plurality of discrete segments is adjacent the bonding device.

5. The method of claim 1 wherein the roller is in tangential communication with the vacuum anvil at the first location.

6. The method of claim 1 wherein transferring each of the plurality of discrete segments comprises drawing a respective discrete segment off of the roller and onto the second continuous web that is on the vacuum anvil, via the vacuum pressure from the vacuum anvil.

7. The method of claim 6 further comprising maintaining the respective discrete segment on the second continuous web via the vacuum pressure from the vacuum anvil, as the vacuum anvil advances the respective discrete segment and the second continuous web from the first location to the second location.

8. The method of claim 1 wherein feeding the first continuous web comprises feeding a web of ear web material; and wherein bonding each of the plurality of discrete segments to the second continuous web comprises bonding discrete ear segments to the second continuous web.

9. The method of claim 1 wherein the vacuum anvil is rotated in a first direction and the roller is rotated in a second direction that is opposite the first direction, with rotation of the roller and the vacuum anvil translating the plurality of discrete segments and the second continuous web, respectively, in the machine direction.

10. The method of claim 9 wherein the vacuum anvil rotates continuously in the first direction and the roller rotates continuously in the second direction, such that the plurality of discrete segments is continuously placed on the second continuous web.

11. The method of claim 1 wherein cutting the first continuous web comprises rotating a knife wheel having at least one knife thereon, with each knife on the knife wheel interacting with the roller to cut the first continuous web when brought into releasable communication with the roller.

12. An apparatus for applying discrete segments to a continuous web, the apparatus comprising:

a roller rotating to translate a first continuous web along a roller surface of the roller, the first continuous web comprising one or more layers;

a vacuum anvil rotating to translate a second continuous web along an anvil surface of the vacuum anvil, the roller and vacuum anvil adjacent to one another at a first location;

at least one cutting element selectively positionable adjacent the roller and that interacts with the roller to cut the first continuous web into a plurality of discrete segments; and a bonding device operable with the vacuum anvil to bond each of the plurality of discrete segments to the second continuous web at a second location downstream from the first location in a machine direction in which the plurality of discrete segments and the second continuous web are translated;

wherein the roller rotates to translate the plurality of discrete segments to the first location, after being cut by the interaction of the at least one cutting element and the roller; and wherein the vacuum anvil generates a vacuum pressure at the anvil surface to cause each of the plurality of discrete segments to transfer from the roller onto the second continuous web at the first location and to be held in place on the second continuous web; and wherein the vacuum anvil comprises:

a plurality of vacuum holes formed in the anvil surface through which the vacuum pressure is communicated; and a plurality of raised protrusions extending out from the anvil surface and that interact with the bonding device to form a pattern of bonds between the second continuous web and respective discrete segments of the plurality of discrete segments.

13. The apparatus of claim 12 wherein the plurality of vacuum holes formed in the anvil surface forms a pattern that generally matches a shape of the discrete segments and a placement location of the discrete segments on the vacuum anvil.

14. The apparatus of claim 12 wherein the plurality of discrete segments comprise acquisition distribution layer segments.

15. The apparatus of claim 12 wherein the plurality of discrete segments comprise ear segments.

16. The apparatus of claim 12 wherein the bonding device comprises a rotary horn that rotates about a central axis.

17. The apparatus of claim 12 wherein the vacuum anvil is configured to rotate in a first direction and the roller is configured to rotate in a second direction that is opposite the first direction, with rotation of the roller and vacuum anvil translating the plurality of discrete segments and the second continuous web, respectively, in the machine direction.

18. The apparatus of claim 12 wherein the second continuous web and a respective discrete segment are transferred to the second location, with the second continuous web adjacent the vacuum anvil and the discrete segment adjacent the bonding device.

19. The apparatus of claim 12 wherein the vacuum pressure at the anvil surface of the vacuum anvil is stronger than a force that retains a respective discrete segment to the roller, such that the respective discrete segment is caused to transfer from the roller onto the second continuous web that is on the vacuum anvil.

* * * * *